United States Patent [19]

Chang et al.

[11] Patent Number: 4,554,075
[45] Date of Patent: Nov. 19, 1985

[54] PROCESS OF DEGRADING CHLORO-ORGANICS BY WHITE-ROT FUNGI

[75] Inventors: Hou-min Chang; Thomas W. Joyce, both of Raleigh, N.C.; Thomas K. Kirk, Madison, Wis.; Van-Ba Huynh, Navarre, Minn.

[73] Assignee: North Carolina State University, Raleigh, N.C.

[21] Appl. No.: 614,980

[22] Filed: May 29, 1984

[51] Int. Cl.$^4$ .............................................. C02F 3/34
[52] U.S. Cl. ................................... 210/611; 210/619; 210/908; 210/909; 435/262
[58] Field of Search ............... 210/611, 619, 620, 908, 210/909; 162/29; 435/262, 267, 911

[56] References Cited

U.S. PATENT DOCUMENTS

| | | | |
|---|---|---|---|
| 2,382,010 | 8/1945 | Hodges | 210/2 |
| 3,660,278 | 5/1972 | Mimura et al. | 210/611 |
| 3,737,374 | 6/1973 | Stern et al. | 210/11 X |
| 3,833,463 | 9/1974 | Croom | 162/29 |
| 3,870,599 | 3/1975 | Azarowicz | 210/611 X |
| 3,876,497 | 4/1975 | Hoffman | 162/189 |
| 3,945,917 | 3/1976 | Foster | 162/29 X |
| 3,962,033 | 6/1976 | Eriksson et al. | 195/8 |
| 4,000,033 | 12/1976 | Nicolle et al. | 162/29 |
| 4,199,444 | 4/1980 | Blair et al. | 210/11 |
| 4,266,035 | 5/1981 | Blair et al. | 435/253 |

OTHER PUBLICATIONS

Gabriel Sundman, T. Kent Kirk & Hou-min Chang; Fungal Decolorization of Kraft Bleach Plant Effluent: Fate of the Chromophoric Material; Mar. 1981; pp. 1-5.
David C. Eaton, Hou-min Chang, Thomas W. Joyce, Thomas W. Jeffries and T. Kent Kirk; The FPL/NCSU Mycor Process for Treatment of Bleach Plant Effluents; Mar. 1981; pp. 1-5.
Alton G. Campbell, Jr. and Thomas W. Joyce; The Removal of Color from Pulp and Paper Mill Effluents by Biological Processes; May 1981; 16 pages.
T. Kent Kirk and Wayne E. Moore; Removing Lignin from Wood with White-Rot Fungi and Digestibility of Resulting Wood; Jan. 1972; pp. 72-79.
T. Kent Kirk, W. J. Connors and J. Gregory Zeikus; Requirement for a Growth Substrate During Lignin Decomposition by Two Wood-Rotting Fungi; Jul. 1976; pp. 192-194.
Knut Lundquist, T. Kent Kirk and William J. Connors; Fungal Degradation of Kraft Lignin and Lignin Sulfonates Prepared from Synthetic $^{14}$C-Lignins; 1977; Arch. Microbiol. 112, pp. 291-296.
Toshio Fukuzumi, Atsumi Nishida, Kiyowo Aoshima and Kyoji Minami; Decolourization of Kraft Waste Liquor with White Rot Fungi I.; Mokuzai Gakkaishi, vol. 23, No. 6, pp. 290-298; 1977.
D. Eaton and H-m., Chang and T. K. Kirk; Fungal Decolorization of Kraft Bleach Plant Effluents; Oct. 1980; pp. 103-106.
David C. Eaton, Hou-min Chang, Thomas W. Joyce, Thomas W. Jeffries and T. Kent Kirk; Method Obtains Fungal Reduction of the Color of Extraction-Stage Kraft Bleach Effluents; Jun. 1982; pp. 89-92.
A. G. Campbell, E. D. Gerrard, T. W. Joyce, and H-m. Chang and T. K. Kirk; The Mycor Process for Color Removal from Bleach Plant Effluent: Bench Scale Studies; Aug./Sep., 1982; pp. 209-214.

Primary Examiner—Thomas Wyse
Attorney, Agent, or Firm—Bell, Seltzer, Park & Gibson

[57] ABSTRACT

A process of degrading chloro-organics contained in liquid waste or effluent utilizes a white-rot fungus as the active ingredient in the chloro-organic degradation. The white-rot fungus is grown in the presence of certain nutrients including nutrient nitrogen and is then caused to enter a secondary metabolic state through nitrogen starvation. The fungus is then immersed in the liquid containing chloro-organics for a time period sufficient for the fungus to degrade the chloro-organics. At least periodically during the degradation period, the fungus is exposed to an oxygen enriched atmosphere. The efficacy and active lifetime of the fungus may be increased by the addition to the liquid of at least one member of the class consisting of nitrogen, a mixture of nutrient minerals, and a biological detergent.

12 Claims, 2 Drawing Figures

PROCESS OF DEGRADING CHLORO-ORGANICS BY WHITE-ROT FUNGI

This invention relates to biological treatment of waste to improve the environmental character thereof, and particularly to the degradation of chloro-organics contained in certain liquid wastes, by-products or effluents by using a white-rot fungus to convert the chloro-organics from aromatics to aliphatics.

BACKGROUND OF THE INVENTION

The discharge of chlorinated organics, particularly chlorophenols, to the environment is a major public health concern. In addition to causing taste and odor problems in potable water supplies, some chloro-organics are believed to be carcinogenic or mutagenic. Because chlorinated organics are inherently recalcitrant to biological degradation, these compounds pass through conventional wastewater treatment plants largely uneffected. To our knowledge, no effective method of biologically degrading chloro-organics has heretofore been recognized or proposed.

There have been recent attempts to use biological processes for treating effluents from papermaking operations to decolorize such effluents. Nova Scotia Research Foundation, Environment Canada, Cooperative Pollution Abatement Research Project Report No. 410-1 (1976). One of these attempts proposes the use of white-rot fungi to decolorize such effluents. Fukuzumi, Nishida, Aoshima, and Minami, *Decolorization of Kraft Waste Liquor with White Rot Fungi* (pt. 1) 23 (6) Journal of the Japan Wood Research Society 290 (1977). However, none of these attempts propose, or to our knowledge even recognize, that white rot fungi will degrade chloro-organics. Since chlorinated organics are used as fungicides, the degradation of chlorinated organics by the fungus was unexpected and surprising.

With the foregoing in mind, it is an object of the present invention to provide an effective process of biologically degrading chloro-organics contained in certain liquids to improve the environmental character thereof.

A more specific object of the present invention is to provide a process of degrading chloro-organics and particularly chlorophenols by using white rot fungi to convert the aromatics to aliphatics.

SUMMARY OF THE INVENTION

The present invention accomplishes these objects by growing a white-rot fungus on the surface of a carrier in the presence of certain nutrients including nitrogen to form a mycelial film on the carrier surface, inducing the fungus into a secondary metabolic state by nitrogen starvation, degrading the chloro-organics contained in a liquid by immersing the fungus while in its secondary metabolic state in the liquid for a sufficient time period for the fungus to convert the aromatics into aliphatics, while at least periodically exposing the fungus to an oxygen enriched atmosphere. It has been determined that the efficacy of the fungus in degrading the chloro-organics and the active lifetime of the fungus may be increased by adding to the liquid containing the chloro-organics a small amount of at least one of a class consisting of nitrogen, a mixture of nutrient minerals, or a biological detergent.

DESCRIPTION OF THE PREFERRED EMBODIMENT

Most microorganisms, including those used in conventional wastewater treatment plants or systems, cannot degrade chlorinated organics and particularly chlorophenols. White-rot fungi, on the other hand, have the capability of degrading such chloro-organics by converting the aromatics to aliphatics. Though the process of this invention can use any of many white-rot fungi, *Phanerochaete chrysosporium* strain BKM F-1767, isolated in east central Russia in 1968, is preferred because of its vigorous growth and rapid degradation of the chloro-organics at the relatively high temperature of 39°–40° C. and because of its formation of abundant conida (asexual spores) which facilitates inoculation and handling.

The first step in the present process is the growing of the white-rot fungus to provide a readily available source of the active ingredient of the chloro-organic degradation process. Such growth should take place under sterile or semi-sterile conditions in a stationary liquid medium containing nitrogen and sufficient basal nutrients for rapid germination and growth.

The following nutrients were used in our experiments in the amounts stated in grams per liter of growth medium:

| Nutrient | Amount |
| --- | --- |
| $KH_2PO_4$ | 2 g/l |
| $MgSO_4.H_2O$ | 0.5 g/l |
| $CaCl_2$ | 0.1 g/l |
| $NH_4Cl$ | 0.12 g/l |
| Thiamine | 0.001 g/l |
| Glucose | 10 g/l |

The temperature of the growth medium should be 30°–40° C., the pH should be 4.0–5.0 and the surrounding atmosphere should have an oxygen content of 20%–100%.

Figure 1:
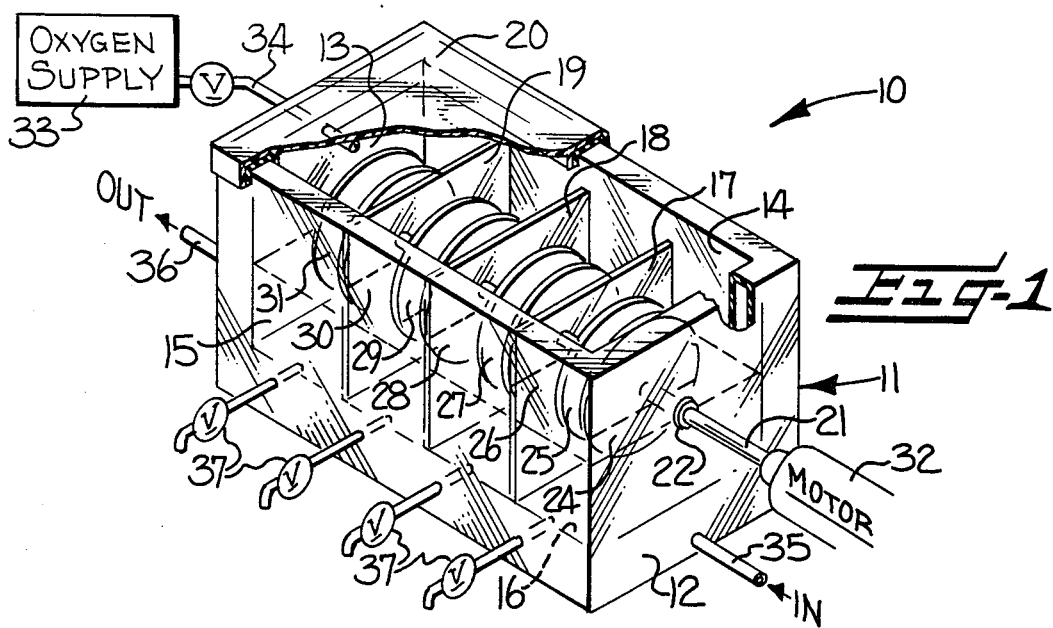
FIG. 1 is a perspective view of one type of reactor that may be used in the practice of the present process.

While any suitable apparatus or equipment for growing the fungus and degrading the chloro-organics may be used, a rotating biological contact reactor has proven to be effective in bench scale experiments and some similar production scale equipment is anticipated to be equally effective when the present process is scaled up to production capacity. Such a rotating biological contact reactor is shown in FIG. 1 and is generally referred to as 10. Reactor 10 offers unique operating features including high surface area per unit volume, low maintenance costs, low energy requirements, simple construction and operation, and commercial availability.

The reactor 10 comprises a tank 11 defined by four walls 12, 13, 14 and 15 and a bottom 16, and three partitions 17, 18 and 19 extend between walls 14 and 15 to divide the tank 11 into four compartments. A cover 20 is provided so that the atmosphere within reactor 10 may be controlled. A shaft 21 is journal for rotation in suitable bearings 22 (only one of which is shown) mounted in walls 12 and 13. Shaft 21 drivingly mounts eight plastic discs 24, 25, 26, 27, 28, 29, 30, and 31 with two discs being located in each of the four compartments of tank 11. A suitable motor 32 is connected to shaft 21 for driving shaft 21 and disc 24-31 in rotation for reasons to be explained.

The reactor 10 may be operated as a batch reactor or as a continuous, plug-flow reactor. The reactor 10 used in our experiments had a capacity of 2.5 liters of liquid being treated. The tank 11 and discs 24-31 were constructed of such size that the discs were 40% submerged in the liquid when tank 11 had 2.5 liters of liquid therein.

An oxygen source 33 is connected to tank 11 above the level of liquid therein by tubing 34 to maintain an oxygen enriched atmosphere, i.e. with an oxygen content higher than air, above the liquid and in contact with 60% of discs 24-31. Preferably, the oxygen content in the atmosphere above the liquid is between about 20% and 100%. The desired temperature of approximately 40° C. is maintained by circulating heated water through a jacket around tank 11 from a source of hot water (not shown) connected to tank 11 by tubing 35 and 36. Suitable drains 37 for removal of the effluent once the chloro-organics have been degraded are connected to each compartment of tank 11.

A carbon/energy source is a nutritional requirement for both fungal growth and degradation of the chloro-organics, and the liquid to be treated does not normally provide such nutritional requirements. Glucose, cellulose, and inexpensive, commercially available, corn syrup work equally well. In fact, our study has demonstrated that primary sludge from a paper mill may be used to provide such nutritional requirements.

To grow the fungus, a spore suspension is inoculated into a growth medium in tank 11 containing growth nutrients at pH 4.5. The spores readily germinate and grow rapidly to form mycelial mats or films on the roughened discs 24-31. During the first two days, the growing mycelium consumes nutrients and attaches to the roughened disc as a thin film. After these first two days, the growth medium is drained from tank 11 and tank 11 is refilled with liquid containing additional growth medium. After two more days of growth, the mycelial mats on discs 24-31 have consumed the available nitrogen and the fungus enters a secondary metabolic state capable of degrading chloro-organics. Throughout this growth period, an oxygen enriched atmosphere has been maintained above the effluent containing growth medium, and the discs have been slowly rotated at a speed at the periphery of preferably 2 feet per minute.

With the fungus in a secondary metabolic state, degradation of chloro-organics contained in a liquid such as effluent or other wastewater can now begin. The rate of degradation is higher at a peripheral speed 2 feet per minute than at 30 feet per minute and consequently a low peripheral speed is preferred during degradation of the chloro-organics. Experiments were conducted with a peripheral speed of 2 feet per minute with excellent results.

The concentration of oxygen in the enclosed space above the liquid in tank 11 is an important factor affecting the rate of degradation of the chloro-organics and the active lifetime of the fungus. Preferably, the oxygen concentration in this atmosphere should be between about 20% and 100% and more preferably between about 50% and 100%.

The degradation of chloro-organics by the white rot fungus was discovered by us during experiments in treating effluents from the first alkaline extraction stage of a chlorine bleach plant from a pulp and papermaking operation. This discovery was made in our efforts to assess the effect of low molecular weight compounds in such effluents on the white rot fungus being used to treat these effluents.

Figure 2:
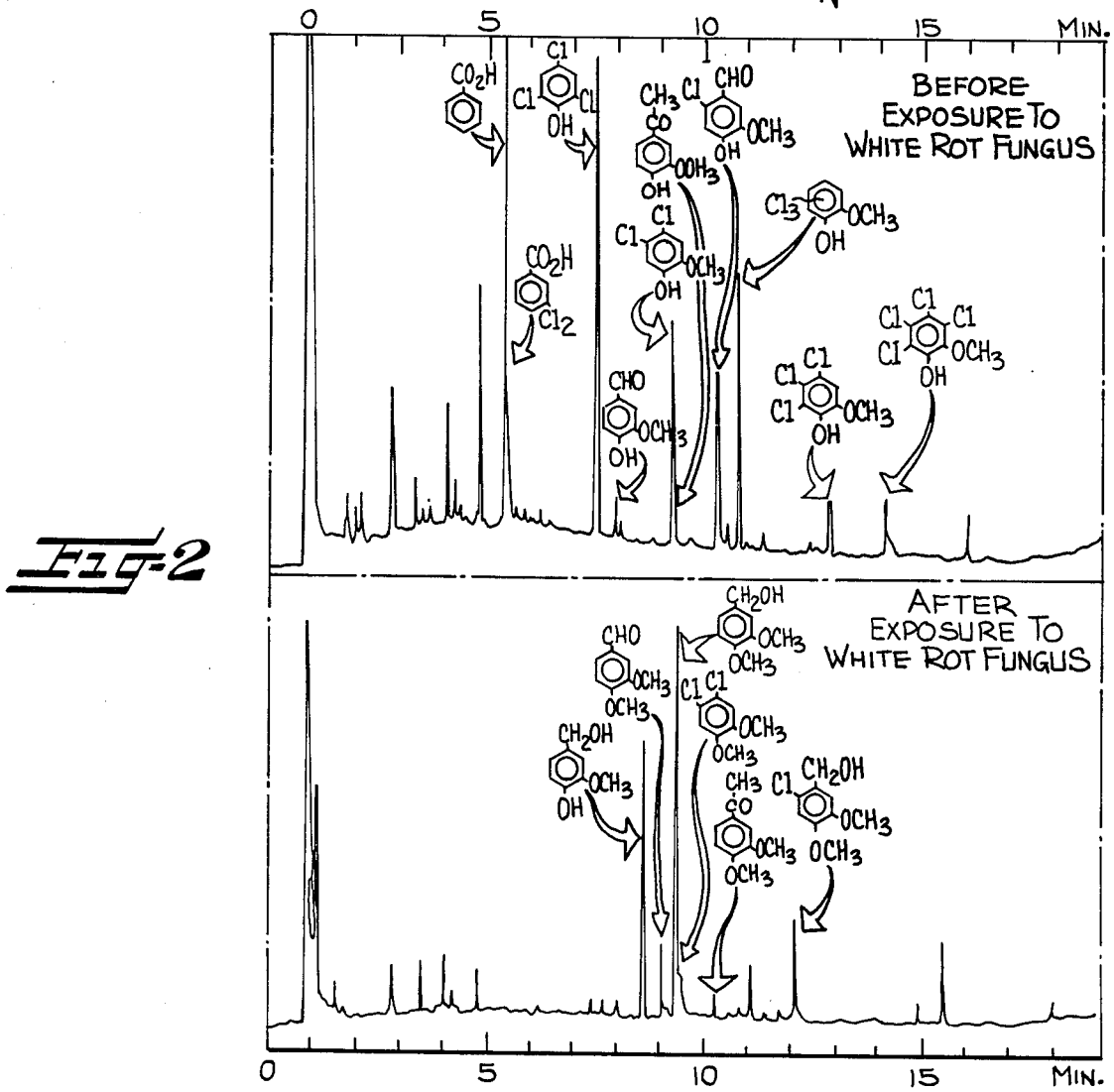
FIG. 2 is a graph of comparative gas chromatograms of effluent before and after exposure to a white-rot fungus.

In making this assessment, the effluents before and after exposure to the white rot fungus were extracted with chloroform after adjusting the pH to 2.5. These extracts were subsequently examined by gas chromatography/mass spectrometry. The gas chromatagrams of the chloroform extracts before and after exposure of the effluents to the white rot fungus and the major components that have been identified by the GC/MS analysis are shown in FIG. 2. Chlorinated phenols were dominant low molecular weight components in the effluents before exposure to the white rot fungus. Surprisingly, these chlorinated phenols were substantially reduced completely disappeared after exposure to the white-rot fungus as is shown in Table 1 below. This result is considered to be highly significant because many of the identified chlorinated phenols are known to be toxic to aquatic life.

In the effluent after exposure to the white rot fungus, veratryl alcohol, a well-known metabolite of the white rot fungus used in these experiments, was the principal product. Other components were veratraldehyde, 6-chloroveratryl alcohol, and vanillyl alcohol. Acetoveratrone and 4,5-dichloroveratrole were also detected. Some of these, like veratryl alcohol, may also be metabolites of the fungus. It is believed that the aromatic compounds found in the effluent before exposure to the white-rot fungus were converted to aliphatic compounds since some aliphatic chlorinated compounds were found to be present in the effluent after exposure to the white-rot fungus.

TABLE 1

Quantitation of chloroform-extractable aromatics obtained from bleach plant effluent (E-1) before and after exposure to the white-rot fungus

| Compound | RTa | Before Exposure ppm | After Exposure ppm |
|---|---|---|---|
| Benzoic acid | 5.40 | 0.12–0.45[b] | none |
| Dichlorobenzoic acid[c] | 5.48 | | none |
| 2,4,6-Triclorophenol | 7.47 | 0.15–0.33 | trace–0.01 |
| Vanillin | 8.05 | 0.01–0.02 | 0.05–0.10 |
| 4,5-Dichloroguaiacol | 9.18 | 0.08–0.25 | trace |
| Acetoguaiacone | 9.22 | trace | none |
| 6-Chlorovanillin | 10.22 | 0.05–0.10 | trace |
| Trichloroguaiacol[c,d] | 10.67 | 0.15–0.34 | trace |
| 5-Chlorovanillin | 11.05 | trace | none |
| 4,5,6-Trichloroguaiacol | 12.74 | 0.04–0.10 | trace |
| Tetrachloroguaiacol | 14.06 | 0.08–0.15 | trace |
| Vanillyl alcohol | 8.67 | none | 0.05–1.20 |
| Veratraldehyde | 9.11 | none | 0.08–1.30 |
| Veratryl alcohol | 9.37 | none | 10–20 |
| 4,5-Dichloroveratrole | 9.59 | none | 0.10–0.30 |
| 4,5,6-Trichloroveratrole | 11.66 | none | trace–0.02 |
| 3,4-Dimethoxyaetophenone | 10.39 | none | trace–0.02 |
| 5-Chloroveratryl alcohol | 11.84 | none | trace |
| 6-Chloroveratryl alcohol | 12.20 | none | 0.50–0.80 |

[a]Retention time on gas chromatogram/capillary column-30M with DB-5 as the liquid phase; oven temperature was held at 60° C. for 1 minute, then programmed at a rate of 15° C./min to 140° C., and 5° C./min. to 255° C.; FID:
[b]Includes dichlorobenzoic acid.
[c]Isomer unknown.
[d]Quantitation of this compound was based on the GC response factor of 4,5,6-trichloroguaiacol.

In our experiments, we discovered that the efficacy and active lifespan of the fungus is markedly increased by the addition of a small amount of nitrogen to the effluent or liquid being treated by the present process. Care must be taken, however, because the addition of too much nitrogen decreases the efficacy thereof and may even cause the fungus to leave its secondary metabolic state and therefore terminate all degradation of the chloro-organics. It has been determined that the addition to the effluent of an amount of nutrient nitrogen ($NH_4Cl$) equal to 20–30% of the original growth nitrogen or about 0.024 to 0.036 grams per liter resulted in a substantive increase in the rate of fungal activity and in the duration of the active lifetime of the fungus.

We have also discovered that the addition to the effluent or liquid of a small amount of nutrient minerals (micro-nutrients or micro-minerals) has a very similar effect to that produced by the addition of nitrogen. It is not known whether all of these minerals are needed or whether some lesser number may be used or whether lower amounts will suffice, but the present invention contemplates the use of only those nutrient minerals which are necessary to produce the desired effect. In our experiments, we used a mixture of nutrient minerals including:

| | |
|---|---|
| Nitrilotriacetic acid | 0.135 g/l |
| $MgSO_4.H_2O$ | 0.27 g/l |
| NaCl | 0.09 g/l |
| $MnSO_4.H_2O$ | 0.045 g/l |
| $CaCl_2$ | 0.007 g/l |
| $FeSO_4.7H_2O$ | 0.009 g/l |
| $ZnSO_4.H_2O$ | 0.009 g/l |
| $CoCl_2.6H_2O$ | 0.009 g/l |
| $CaSO_4.5H_2O$ | 0.0009 g/l |
| $Na_2MO_4.2H_2O$ | 0.0009 g/l |
| $AlK(SO_4)_2.12H_2O$ | 0.0009 g/l |
| $H_3BO_3$ | 0.0009 g/l |
| Total | 0.58 g/l |

Also, the addition to the effluent or liquid of a small amount of detergent, i.e., 0.3% by volume, produces a marked increase in the efficacy and active lifetime of the fungus. An illustrative example of such a biological detergent is a complex of polyoxyethylene ethers of mixed partial oleic esters of sorbital anhydrides sold under the brand name "Tween-80" by Fisher Scientific Company.

The greatest improvement in efficacy and active lifetime of the fungus were achieved when both a mixture of nutrient minerals and a detergent were added to the effluent or liquid. Surprisingly, the effect of the minerals and of the detergent were additive, producing up to a fourfold increase. This additive effect was not realized when nitrogen and minerals were added to the effluent nor when nitrogen and detergent were added.

In the drawings and specifications, there have been set forth preferred embodiments of the invention, and although specific terms are employed, they are used in a generic and descriptive sense only and not for purposes of limitation.

That which is claimed is:

1. A process of degrading chloro-organics contained in certain liquids to improve the environmental character thereof comprising the steps of:
   (a) providing a white-rot fungus which is in a secondary metabolic state, and
   (b) degrading the chloro-organics in the liquid by immersing the white-rot fungus in the liquid for a sufficient time period, while at least periodically
   (c) exposing the fungus to oxygen.

2. A process according to claim 1 wherein the step of providing a white-rot fungus comprises growing the white-rot fungus under environmental conditions promoting rapid growth and inducing the fungus to enter the secondary metabolic state through nitrogen starvation.

3. A process according to claim 1 wherein the chloro-organics are degraded by being converted from aromatics to aliphatics by the action of the white-rot fungus.

4. A process according to claim 3 wherein the white rot fungus is *Phanerochaete chrysosporium*.

5. A process of degrading chloro-organics contained in certain liquids to improve the environmental character thereof comprising the steps of:
   (a) growing a white-rot fungus on the surface of a carrier in the presence of certain nutrients including nitrogen to form a mycelial film thereon,
   (b) causing the white-rot fungus to enter a secondary metabolic state through nitrogen starvation,
   (c) degrading chloro-organics contained in a liquid by converting such chloro-organics from aromatics to aliphatics by immersing at least a portion of the carrier having the white-rot fungus thereon in the liquid for a sufficient time period for the fungus to degrade the chloro-organics, while at least periodically
   (d) exposing the fungus to oxygen.

6. A process according to claim 5 wherein the step of exposing the fungus to oxygen comprises exposing the fungus to an atmosphere containing between about 20% and 100% oxygen.

7. A process according to claim 5 wherein the carrier is rotatable, is partially immersed in the liquid and is slowly rotated to sequentially immerse the fungus in the liquid and expose the fungus to the oxygen enriched atmosphere.

8. A process according to claim 5 including the step of
   (e) adding to the liquid containing the chloro-organics at least one member of the class consisting of nutrient nitrogen, a mixture of nutrient minerals, and a detergent in an amount sufficient to increase the efficacy and prolong the active life of the fungus but insufficient to cause the fungus to depart from its secondary metabolic state.

9. A process of degrading chloro-organics contained in certain liquids to improve the environmental character thereof comprising the steps of:
   (a) growing a white-rot fungus on the surface of a rotatable carrier in the presence of certain nutrients including nutrient nitrogen to form a mycelical film on such surface,
   (b) causing the white-rot fungus to enter a secondary metabolic state through nitrogen starvation,
   (c) degrading chloro-organics contained in a liquid by converting such chloro-organics from aromatics to aliphatics by partially immersing the fungus in the liquid for a sufficient time period for the fungus to degrade the chloro-organics while
   (d) slowly rotating the carrier to sequentially immerse the fungus in the liquid and expose the fungus to an atmosphere containing between about 20% and 100% oxygen, and (e) adding to the liquid containing the chloro-organics at least one member of the class consisting of nutrient nitrogen, a mixture of nutrient minerals, and a detergent in an amount sufficient to increase the efficacy and prolong the active life of the fungus but insufficient to cause the fungus to depart from its secondary metabolic state.

10. A process according to claim 9 wherein a mixture of nutrient minerals and a detergent are added to the liquid to further increase the efficacy of the fungus in degrading the chloro-organics.

11. A process according to claim 9 wherein the chloro-organics degraded are chlorophenols.

12. A process according to claim 9 wherein the white rot fungus is *Phanerochaete chrysosporium*.

* * * * *